(12) United States Patent
Hijlkema et al.

(10) Patent No.: US 11,357,931 B2
(45) Date of Patent: Jun. 14, 2022

(54) MESH FOR USE IN A NEBULISER, AND A METHOD OF MANUFACTURING THE SAME

(71) Applicant: KONINKLIJKE PHILIPS N.V., Eindhoven (NL)

(72) Inventors: Markus Hijlkema, Chichester (GB); John Nigel Pritchard, Leicester (GB); Renatus Hendricus Maria Sanders, Roermond (NL); Johannes Christiaan Van Der Schaft, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1208 days.

(21) Appl. No.: 14/906,371

(22) PCT Filed: Jul. 15, 2014

(86) PCT No.: PCT/IB2014/063121
§ 371 (c)(1),
(2) Date: Jan. 20, 2016

(87) PCT Pub. No.: WO2015/011608
PCT Pub. Date: Jan. 29, 2015

(65) Prior Publication Data
US 2016/0158464 A1    Jun. 9, 2016

(30) Foreign Application Priority Data
Jul. 22, 2013 (EP) .................................. 13306051

(51) Int. Cl.
*A61M 11/00* (2006.01)
*B05B 17/00* (2006.01)
(Continued)

(52) U.S. Cl.
CPC ......... *A61M 11/003* (2014.02); *A61M 11/005* (2013.01); *A61M 15/0021* (2014.02);
(Continued)

(58) Field of Classification Search
CPC .. A61M 11/00; A61M 11/001; A61M 11/002; A61M 11/003; A61M 11/005;
(Continued)

(56) References Cited

U.S. PATENT DOCUMENTS

| 3,747,120 A | 7/1973 | Stemme |
| 5,133,343 A | 7/1992 | Johnson et al. |

(Continued)

FOREIGN PATENT DOCUMENTS

| CN | 102470225 A | 5/2012 |
| CN | 103189087 A | 7/2013 |

(Continued)

OTHER PUBLICATIONS

Yamamoto, Formal Translation of Japanese Patent Publication No. S59-52562 A, Oct. 2019 (Year: 2019).*

(Continued)

*Primary Examiner* — Elliot S Ruddie
(74) *Attorney, Agent, or Firm* — Daniel H. Brean; Andrew M. Gabriel

(57) ABSTRACT

There is provided a mesh for use in forming droplets of liquid in a nebuliser, the mesh comprising a first portion (22) made of a first material having a plurality of holes passing therethrough; and a second portion (26) made of a second material that is in contact with the first portion (22), the second portion (26) having a corresponding plurality of holes passing therethrough, the plurality of holes in the second portion forming nozzles (28) for an outlet side of the mesh; wherein the first material has a higher density than the second material.

12 Claims, 16 Drawing Sheets

(51) Int. Cl.
*A61M 15/00* (2006.01)
*A61M 15/02* (2006.01)

(52) U.S. Cl.
CPC ..... *B05B 17/0638* (2013.01); *A61M 15/0085* (2013.01); *A61M 15/025* (2014.02); *A61M 2207/00* (2013.01)

(58) Field of Classification Search
CPC .. A61M 11/02; A61M 11/041; A61M 11/042; A61M 11/06; A61M 11/065; A61M 11/08; A61M 15/00; A61M 15/0021; A61M 15/025; A61M 15/0085; A61M 2207/00; B05B 17/00; B05B 17/04; B05B 17/06; B05B 17/0607; B05B 17/0615; B05B 17/0638; B05B 17/0646; B41J 2/14; B41J 2/14016; B41J 2/1433
USPC ...... 128/200.14, 200.16; 347/44, 45, 46, 47, 347/65
See application file for complete search history.

(56) References Cited

U.S. PATENT DOCUMENTS

| | | | |
|---|---|---|---|
| 5,261,601 A | 11/1993 | Ross et al. | |
| 5,487,378 A * | 1/1996 | Robertson | A61M 15/0065 128/200.14 |
| 6,722,582 B2 | 4/2004 | Hess et al. | |
| 8,739,777 B2 | 6/2014 | Krentzmann et al. | |
| 9,486,593 B2 | 11/2016 | Merassi | |
| 2002/0130925 A1 | 9/2002 | Koeda | |
| 2005/0190231 A1* | 9/2005 | Lim | B41J 2/1642 347/45 |
| 2008/0094432 A1 | 4/2008 | Silverbrook | |
| 2008/0128387 A1 | 6/2008 | Chen | |
| 2009/0273633 A1 | 11/2009 | Silverbrook | |
| 2012/0285447 A1* | 11/2012 | Schipper | A61B 5/1117 128/200.16 |
| 2013/0280431 A1* | 10/2013 | Sambhy | C09D 183/10 427/379 |
| 2013/0334339 A1* | 12/2013 | Xu | C25D 5/54 239/102.1 |
| 2014/0145000 A1 | 5/2014 | Verschueren | |

FOREIGN PATENT DOCUMENTS

| | | | |
|---|---|---|---|
| EP | 0099730 A2 | 2/1984 | |
| JP | 59052562 | 3/1984 | |
| JP | S6054761 A | 3/1985 | |
| JP | S5952562 A1 * | 12/1987 | ............. B05B 17/06 |
| JP | 2005296737 | 10/2005 | |
| RU | 2007115030 A | 10/2008 | |
| RU | 107026 U1 | 8/2011 | |

OTHER PUBLICATIONS

Lin, Chun-You et al., "An Ultrasonic Aerosol Therapy Nebulizer Using Electroformed Palladium—Nickel Alloy Nozzle Plates", ScienceDirect, Sensors and Actuators A: Physical, 169, (2011), pp. 187-193.

* cited by examiner

MESH FOR USE IN A NEBULISER, AND A METHOD OF MANUFACTURING THE SAME

CROSS-REFERENCE TO RELATED APPLICATIONS

This patent application claims the priority benefit under 35 U.S.C. § 371 of international patent application no. PCT/IB2014/063121, filed Jul. 15, 2014, which claims the benefit of European Patent Application No. EP13306051.7, filed on Jul. 22, 2013, the contents of which are herein incorporated by reference.

TECHNICAL FIELD OF THE INVENTION

The invention relates to a mesh for use in a nebuliser that nebulises a liquid stored therein into fine droplets, and in particular relates to a mesh having a plurality of nozzles with an exit diameter within a required range and to a method of manufacturing such a mesh, as well as to a nebulizer.

BACKGROUND TO THE INVENTION

Nebulisers, or atomisers as they are sometimes called, are devices that generate a fine spray or aerosol from a liquid. A particularly useful application for nebulisers is to provide a fine spray containing a dissolved or a suspended particulate drug for administration to a patient by inhalation.

Piezo-mesh based nebulisers (one type of which uses a "flat plate" geometry of a piezoelectric element and a mesh to produce aerosol) are commonly used to generate aerosols in such drug delivery apparatus, whereby a piezoelectric element vibrates the liquid through a mesh to produce the fine aerosol spray. The mesh contains a large number of small nozzles or holes (e.g. 5000-15000) through which the liquid can pass to form the droplets. The mesh is also known as a nozzle plate, aperture plate or a membrane.

FIG. 1 shows an exemplary nebuliser 2. The nebuliser 2 comprises a body 4 having an inlet 6 and an outlet 8 arranged so that when a user of the nebuliser 2 inhales through the outlet 8, air is drawn into and through the nebuliser 2 via the inlet 6 and outlet 8 and into the user's body. The outlet 8 is typically provided in the form of a mouthpiece or a facial or nasal mask or in a form that is suitable for connection to a separate replaceable mouthpiece or facial or nasal mask.

The nebuliser 2 comprises a nebulisation chamber 10 between the inlet 6 and outlet 8 for storing a liquid 12, for example a medication or drug, to be nebulised (i.e. to be turned into a fine mist or spray). The nebuliser 2 is configured such that the fine droplets of liquid 12 combine with the air drawn through the nebuliser 2 when the user inhales to deliver a dose of the medication or drug to the user.

An actuator 14 such as a piezoelectric element is provided along one wall of the nebulisation chamber 10 to agitate or vibrate the liquid 12 stored in the nebulisation chamber 10. A mesh 16 is positioned in the nebulisation chamber 10 opposite the actuator 14 with liquid 12 to be nebulised being held in the cavity between the actuator 14 and the mesh 16. The mesh comprises a large number of nozzles through which the liquid 12 can pass to form the droplets. The mesh 16 has an inlet side 18 that faces the liquid 12 and actuator 14 and an outlet side 20 opposite the inlet side 18 from which the droplets of liquid 12 emerge.

Although not shown in FIG. 1, the nebuliser 2 may also comprise a reservoir that holds further liquid 12 to be nebulised and that is connected to the nebulisation chamber 10 so that the required amount of liquid 12 is maintained in the nebulisation chamber 10.

The actuator 14 is operated to create ultrasonic pressure waves in the liquid 12 which push the liquid 12 through the nozzles in the mesh 16 to form the droplets.

Since a patient typically has to administer a certain amount of medication in a particular treatment dose, the treatment time is mainly determined by the mass flow rate of the droplets generated by the nebuliser. Particularly for new medications, such as biologics, where the medication dose can be large, treatment time can be up to several hours with currently available nebulisers.

In order for a medicine to be therapeutically effective when inhaled, and in particular for the medicine to be deposited in the lungs, the aerosol droplet size of the medicine must be within a narrow therapeutic range. The size of the droplets determines in which part of the lungs the medicine is deposited. The graph in FIG. 2 shows how particle size affects the percentage deposition in the mouth and throat, the airways and the alveolar region.

It can be seen from FIG. 2 that there is a size window of 1-5 µm if the medication is to be deposited deep in the lungs and deposition in the mouth and throat is to be minimised. For many medical applications, a Mass Median Diameter (MMD) of 5 µm is considered as an upper limit for the droplets of liquid. An MMD of 5 µm means that 50% of the medication is contained in droplets smaller than 5 µm.

The size of the droplets formed by the mesh is determined by the exit diameter of the nozzle (i.e. the diameter of the nozzle on the side of the mesh that droplets emerge—i.e. the outlet side 20 of the mesh 16 in the nebuliser 2 of FIG. 1). The droplet diameter is roughly twice the exit diameter of the nozzle d as shown in FIG. 3. This means that a mesh 16 should typically have nozzles with an average exit diameter of 2.5 µm.

In a simplified model, every nozzle creates a single droplet during each cycle of the actuator 14. Thus bigger droplets will result in a higher mass flow out of the nebuliser 2.

For a robust product, the product to product variation of aerosol mass flow rate at a certain actuator vibration frequency should be low. Specifying a limit on this output variation thus has an implication for the acceptable variation in the nozzle exit diameter.

In one example, it is assumed that a variation of +/−25% in the mass flow rate is acceptable. If it is assumed that a single droplet is created per nozzle with every pressure wave, then the mass flow rate depends on droplet volume $V_{drop}$ which depends on the third power of nozzle exit diameter d (with $V_{drop}=(4\pi/3)\cdot(d/2)^3$). A 25% change in the mass of a droplet thus corresponds to a 7.7% change in droplet diameter.

Suppose it is assumed that the aerosol output in terms of grams per minute of liquid is 1.64 (90%) standard deviations within the specification limit. The standard deviation that is allowed on the droplet size, $\sigma_{drop}$, is then 7.7/1.64=4.7%. If it is assumed that the drop diameter $d_{drop}$ is equal to the nozzle exit diameter d multiplied by some constant c, then $\sigma_{drop}^2=c^2\cdot\sigma_{nozzle}^2$. Thus, assuming that a 4.5 µm diameter droplet is generated by a nozzle having a 2.5 µm exit diameter, then 2.6% is obtained, that is a 0.065 µm variation in the nozzle exit diameter d. Thus, there is a tight tolerance on the nozzle exit diameter d.

In addition to the tight tolerance on the nozzle exit diameter d, the mesh 16 needs to have a certain mass per unit area for efficient operation. The mass of the mesh 16 needs to be considered where the thickness of the mesh 16 (denoted $t_{mesh}$ in FIG. 1) is much smaller than the separation of the mesh 16 from the actuator 14 (denoted $t_{separation}$ in FIG. 1). If the pressure waves generated by the actuator 14 are reflected by the mesh 16 back to the actuator 14, a resonant cavity is created. The reflected pressure wave helps to increase the pressure further, keeping energy in the system, which results in less energy needing to be input to the liquid by the actuator 14. In some cases, a mesh 16 with a mass per unit area of 0.04 gram/cm² is sufficient to create this resonant cavity.

However, this mass per unit area of the mesh 16 can normally only be achieved by forming the mesh 16 from a high density metal such as stainless steel, platinum or nickel palladium due to the additional constraint that the thickness of the mesh 16 should be small.

Thus, a problem exists in that a mesh 16 should be produced with a tight tolerance on nozzle exit diameter and with sufficient mass per unit area of the mesh to create a resonant cavity. In addition, the cost of producing the mesh 16 should be low, as the mesh 16 is typically a replaceable part of the nebuliser. Current products in the market use electroformation (using platinum or nickel palladium) or laser-drilling (in stainless steel) to produce the mesh 16. However, the required nozzle exit diameter and the variation on this diameter are difficult to achieve using these techniques, resulting in a low yield from the manufacturing process and a high cost if the 0.065 μm standard deviation is to be achieved.

SUMMARY OF THE INVENTION

Therefore, there is a need for a mesh that has a tight tolerance on nozzle exit diameter and the mass per unit area of the mesh required to create a resonant cavity that can be manufactured at lower cost through a higher yield manufacturing process.

The object of the present invention is solved by the subject-matter of the independent claims, wherein further embodiments are incorporated in the dependent claims. It should be noted that the following described aspects of the invention apply also for the mesh for use in forming droplets of liquid in a nebuliser and for the method of manufacturing a mesh for use in forming droplets of liquid in a nebuliser.

It has been found that it is possible to achieve the tight tolerance on nozzle exit diameter in other types of materials using inherently more-accurate manufacturing methods. For example, chemically etching nozzles in silicon or laser-etching nozzles in a polymer can meet the required tolerances, but meshes made from these materials are not dense enough to fulfil the mass requirement.

Thus, in accordance with the invention, there is provided a mesh that comprises a hybrid geometry in which the useful properties from two different types of material are combined to form the mesh. In particular, part of the mesh is made from a first material that provides the required mass per unit area of the mesh, and another part of the mesh is made from a second material (having a lower density than the first material) that is used to form the nozzles having the required exit diameter.

In particular, according to a first aspect of the invention, there is provided a mesh for use in forming droplets of liquid in a nebuliser, the mesh comprising a first portion made of a first material having a plurality of holes passing therethrough; and a second portion made of a second material that is in contact with the first portion, the second portion having a corresponding plurality of holes passing therethrough, the plurality of holes in the second portion forming nozzles for an outlet side of the mesh; wherein the first material has a higher density than the second material.

According to an example, the plurality of holes in the first portion made of the first material are first openings forming inlet openings of the mesh. The plurality of holes in the second portion made of the second material are second openings forming the nozzles with outlet openings of the mesh. The second portion provides transition portions between the inlet openings and the outlet openings. The outlet openings are smaller than the inlet openings.

According to an example, the second openings forming the nozzles are having a tapered cross-section with a decreasing width in flowing direction. The second material is provided with an increasing material thickness forming the nozzle openings.

According to an example, the plurality of holes in the first portion made of the first material are provided with a first hole geometry having a first opening size. The plurality of holes in the second portion made of the second material are provided with a second hole geometry having a second opening size. The second opening size is smaller than the first opening size. The plurality of the holes in the first portion provide first supply openings, and the plurality of holes in the second portion provide the nozzles as second outlet openings that are arranged stream-downwards from the first supply openings.

According to an example, the first material is a material having a density that is greater than 8 g/$cm^3$ and/or less than 22 g/$cm^3$.

According to an example, the first material can be a metal or a metal alloy. In particular the first material can be stainless steel, platinum, cobalt, gold, tungsten or nickel palladium.

According to an example, the second material is a material having a density that is greater than 0.8 g/$cm^3$ and/or less than 3 g/$cm^3$.

According to an example, the second material can be silicon, a polymer or an epoxy. In particular the second material can be polycarbonate, polyimide or Epo-tek® 353ND.

In an example, each nozzle has a diameter that is within a predetermined range at the outlet side of the mesh.

According to an example, the plurality of holes in the second portion have a diameter that tapers from a diameter that is generally the same as the diameter of the holes in the first portion to a smaller diameter that is within a predetermined range at the outlet side of the mesh.

The second material of the second portion thus contributes to forming the nozzle to a larger amount than the first material. Simply said, the first material is used for providing the basic structure, but the second material is used for providing the exact shape, dimensions and position of the nozzles.

In some embodiments the first portion is a layer or plate of the first material.

In some embodiments the second portion is a layer or plate of the second material.

In some embodiments the layer or plate of the second material is bonded or attached to the layer or plate of the first material.

In alternative embodiments the second portion comprises second material located in the holes of the first portion.

In some embodiments the plurality of holes in the first portion have a generally uniform diameter or a diameter that tapers from a diameter at an inlet side of the mesh to a smaller diameter at the other side of the first portion.

According to an example, the first material is provided as a layer or plate comprising the plurality of holes, and the second material is provided as a plurality of inlays that are least partly located in the holes of the first portion, each inlay at partly filling one of the holes in the first material, and having the nozzles formed in the second material.

According to an example, the first material is provided as a first layer or plate comprising the plurality of holes, and the second material is provided as a second layer or plate, in which the nozzles are formed.

According to an example, the first portion preferably has sufficient mass to create a resonant cavity in the nebuliser.

According to an example, additionally or alternatively, the first portion has a mass per unit area of at least 0.04 gram/cm$^2$.

According to a second aspect of the invention, there is provided a nebuliser comprising a mesh as described above.

According to an example, the nebulizer comprises a body having an inlet and an outlet arranged so that when a user of the nebuliser inhales through the outlet, air is drawn into and through the nebuliser via the inlet and outlet and into the user's body. The outlet may be provided in the form of a mouthpiece or a facial or nasal mask or in a form that is suitable for connection to a separate replaceable mouthpiece or facial or nasal mask. Further, a nebulisation chamber is provided between the inlet and outlet for storing a liquid. The nebuliser is configured with a mesh as described before, such that the fine droplets of liquid combine with the air drawn through the nebuliser when the user inhales to deliver a dose of the medication or drug to the user.

According to a third aspect of the invention, there is provided a method of manufacturing a mesh for use in forming droplets of liquid in a nebuliser, the method comprising a step a) providing a first portion made of a first material having a plurality of holes formed therethrough; and a step b) using a second portion made of a second material that has a lower density than the first material to form nozzles for an outlet side of the mesh, the second portion being placed in contact with the first portion, the second portion having a corresponding plurality of holes formed therethrough.

In an example, the first material is a material having a density that is greater than 8 g/cm$^3$ and/or less than 22 g/cm$^3$. The first material can be a metal or a metal alloy. In particular the first material can be stainless steel, platinum, cobalt, gold, tungsten or nickel palladium.

According to an example, the step of providing a first portion made of a first material having a plurality of holes formed therethrough comprises
a1) providing a first portion made of the first material; and
a2) forming a plurality of holes through the first portion.

In some embodiments the step of forming a plurality of holes through the first portion comprises using laser drilling.

In alternative embodiments the step of providing a first portion comprises using electroformation.

In an example, the second material is a material having a density that is greater than 0.8 g/cm$^3$ and/or less than 3 g/cm$^3$. The second material can be silicon, a polymer or an epoxy. In particular the second material can be polycarbonate, polyimide or Epo-tek® 353ND.

In some embodiments the plurality of holes formed through the second portion are formed using chemical etching, laser etching or laser drilling.

According to an example, the step of providing a first portion made of the first material having the plurality of holes formed therethrough comprises:

providing the plurality of holes in the first portion made of the first material as first openings forming inlet openings of the mesh.

The step of using a second portion made of the second material having the plurality of holes formed therethrough comprises:

providing the plurality of holes in the second portion made of the second material as second openings forming the nozzles with outlet openings of the mesh.

The second portion provides transition portions between the inlet openings and the outlet openings. Further, the outlet openings are smaller than the inlet openings.

According to an example, in step b), the second openings forming the nozzles are provided having a tapered cross-section with a decreasing width in flowing direction; and, in step b), the second material is provided with an increasing material thickness forming the nozzle openings.

According to an example, in step a), the plurality of holes in the first portion made of the first material are provided with a first hole geometry having a first opening size. In step b), the plurality of holes in the second portion made of the second material are provided with a second hole geometry having a second opening size; wherein the second opening size is smaller than the second opening size.

In step a), the plurality of the holes in the first portion provides first supply openings.

In step b), the plurality of holes in the second portion provides the nozzles as second outlet openings that are arranged stream-downwards from the first supply openings.

In some embodiments the step of providing a first portion comprises providing a layer or plate of the first material.

According to an example, the first material is provided as a layer or plate comprising the plurality of holes; and the second material is provided as a plurality of inlays that are least partly located in the holes of the first portion, each inlay at partly filling one of the holes in the first material, and having the nozzles formed in the second material.

According to an example, the step of using a second portion to form nozzles for an outlet side of the mesh comprises:
b1) providing a layer or plate of the second material;
b2) forming the corresponding plurality of holes in the second material; and
b3) bonding or attaching the first portion to the second portion.

According to an alternative example, the step of using a second portion to form nozzles for an outlet side of the mesh comprises:
b4) filling the plurality of holes in the first portion with the second material; and
b5) forming the plurality of nozzles in the second material.

Preferably the first portion has sufficient mass to create a resonant cavity in the nebuliser.

Preferably the first portion has a mass per unit area of at least 0.04 gram/cm$^2$.

These and other aspects of the present invention will become apparent from and be elucidated with reference to the embodiments described hereinafter.

BRIEF DESCRIPTION OF THE DRAWINGS

Exemplary embodiments of the invention will now be described, by way of example only, with reference to the following drawings, in which.

DETAILED DESCRIPTION OF EXEMPLARY EMBODIMENTS

Figure 1:
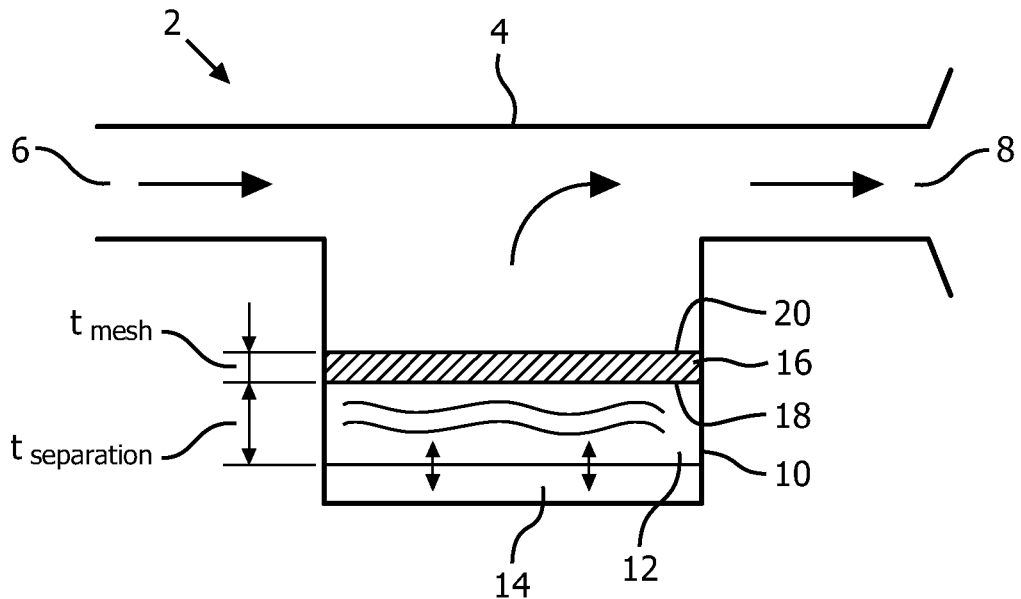
FIG. 1 is a block diagram of an exemplary nebuliser comprising a nozzle plate.
Figure 2:
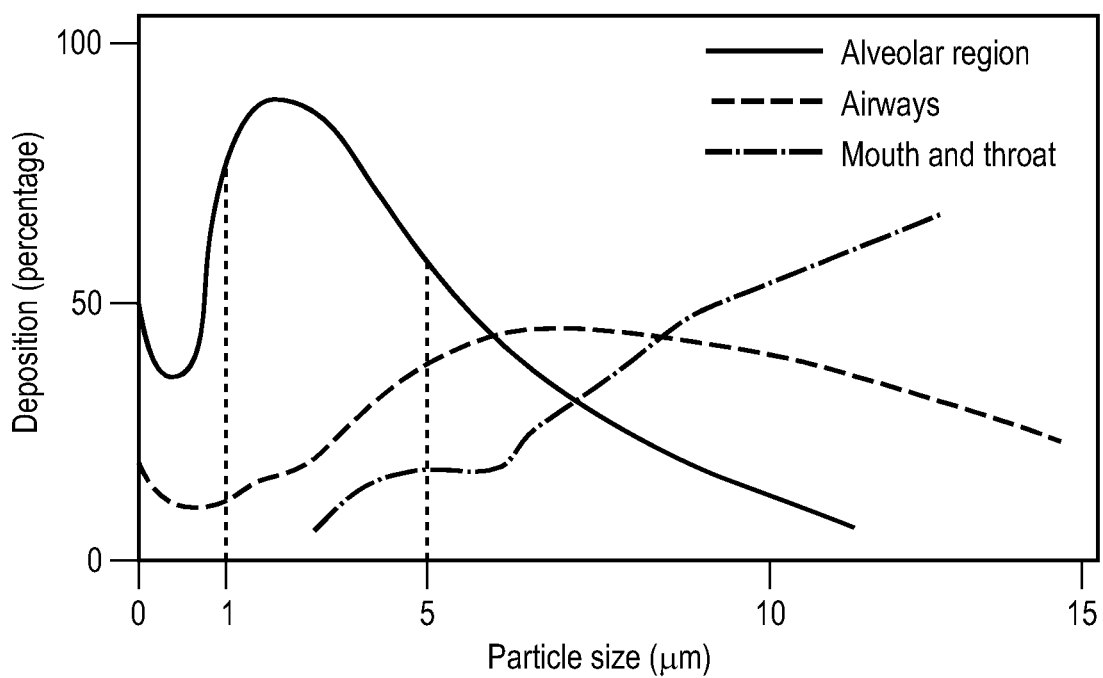
FIG. 2 is a graph illustrating the relationship between particle size and the percentage deposition of particles in different parts of the body.
Figure 3:
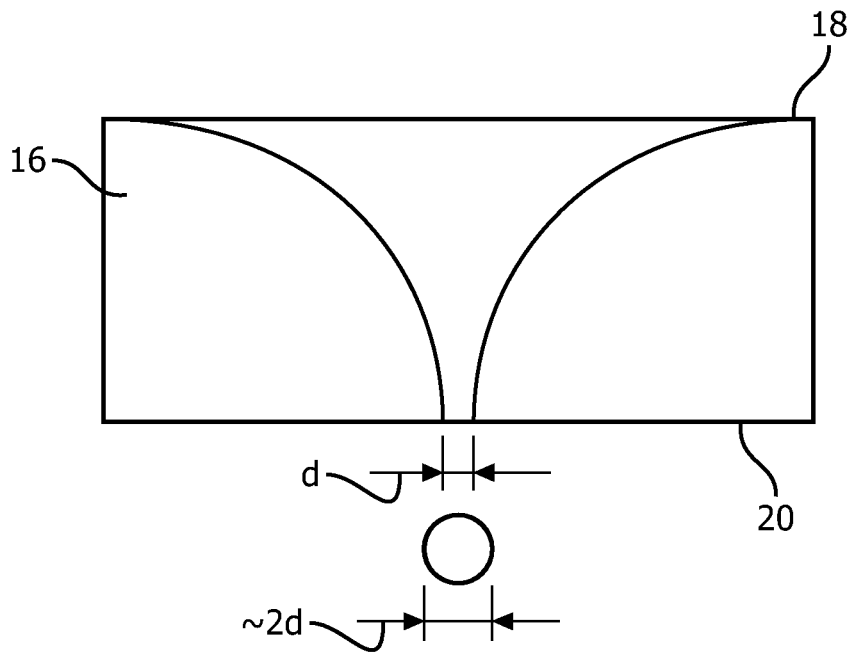
FIG. 3 is an illustration of the relationship between nozzle exit diameter and droplet size.

Although the invention is described below with reference to a piezo-mesh based nebuliser for use in generating an aerosol from a medication as shown in FIG. 1, it will be appreciated that the invention is applicable to other types of product that nebulise a liquid, for example air humidifiers, shavers, steam irons and perfume dispensers. The mesh 16 used in the nebuliser 2 is also known in the art as a nozzle plate, aperture plate and a membrane.

As noted above, to address the problems with current techniques for manufacturing meshes (in particular techniques that use electroformation or laser-drilling) which provide a low yield from the manufacturing process and a high cost, the invention provides a mesh 16 that comprises a hybrid geometry in which the useful properties from two different types of material (which in some cases arise from the fabrication techniques that can be used) are combined to form the mesh 16. In particular, part of the mesh 16 is made from a first material, such as a metal or metal alloy, that provides the required mass per unit area of the mesh 16, and another part of the mesh 16 is made from a second material having a lower density than the first material, with the second material being used to form at least the part of the nozzles at the outlet side 20 of the mesh 16. The second material is selected so that manufacturing techniques can be used that allow nozzles to be created with the required exit diameter within the required tolerance (and that result in a much higher yield than conventional techniques).

Figure 4:
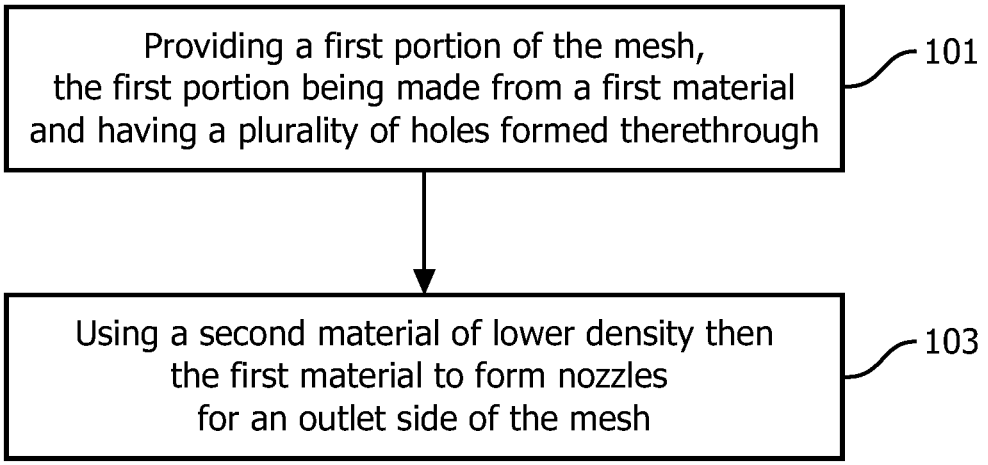
FIG. 4 is a flow chart illustrating a general method of manufacturing a mesh according to the invention.

In an example, as shown in FIG. 4, a method of manufacturing a mesh for use in forming droplets of liquid in a nebuliser is provided, the method comprising:

a) providing 101 a first portion made of a first material having a plurality of holes formed therethrough; and b) using 103 a second portion made of a second material that has a lower density than the first material to form nozzles for an outlet side of the mesh, the second portion being placed in contact with the first portion, the second portion having a corresponding plurality of holes formed therethrough.

It is noted that FIG. 4 also shows further aspects as options of the method.

FIG. 4 illustrates an example of the method of manufacturing or fabricating a mesh 16 according to the invention. The first step, step 101, comprises providing a first portion of the mesh 16. The first portion is typically in the form of a layer or substrate. The first portion is made from a first material that has a sufficient density to allow the mass requirement of the mesh 16 to be met (i.e. sufficient density to enable the first portion—after the holes have been formed—to have a mass per unit area of at least 0.04 gram/cm$^2$). The first material can be a metal or a metal alloy, for example stainless steel, platinum, cobalt, gold, tungsten or nickel palladium. In general, materials having a density greater than 8 g/cm$^3$ and/or less than 22 g/cm$^3$ are suitable for use in forming the first portion of the mesh 16. In an example, materials having a density in the range of 8 to 22 g/cm$^3$ are used for forming the first portion of the mesh 16.

The first portion provided in step 101 also has a plurality of holes formed therethrough. As noted above, a mesh 16 can typically have between 5000-15000 holes or nozzles therein, although it will be appreciated that a different number of holes can be formed in the first portion as required for the mesh 16. The holes can be of any suitable shape, such as circular, generally circular, elliptical, rectangular, etc.

The technique used in step 101 to form the first portion with the plurality of holes can depend on the material the first portion is made of. For example, where the first portion is made from stainless steel, step 101 can comprise providing a stainless steel layer or sheet and using laser-drilling to form the holes.

An alternative technique that can be used in step 101 is electroformation using electroplating. Electroplating is a process that uses electrical current to reduce dissolved metal cations so that they form a coherent metal coating on an electrode. Electroforming uses electroplating to build structures with particular shapes on a substrate electrode, which is then separated from the electrode. In particular, a metal layer is grown on the substrate electrode, and using a non conductive layer like a polymer resist, areas can be selected that are shielded off from the metal growth. Thus a metal structure is grown that has holes filled with non-conductive material, which is then removed to open up the holes to provide first portion.

As the exit of the nozzles at the outlet side 20 of the mesh 16 will be formed from a second material, there is no need for the diameter of the holes in the first portion to be particularly precise. However, a minimum diameter of, for example, 15 µm is set by the resistance a liquid flowing through a small channel will experience. The maximum diameter is a choice determined by the density of holes in the mesh (i.e. the number of holes per unit area in the inlet side 18 of the mesh 16) that is targeted, and would typically be 20 µm if the aim was to achieve a mesh 16 with 5000-15000 nozzles with the thickness of the mesh being smaller than 100 µm.

Regarding the density of the holes in the mesh 16 (i.e. the number of holes per unit area in the inlet side 18 of the mesh 16), it will be appreciated that increasing the density and/or the diameter of holes in the mesh 16 reduces the overall mass per unit area, and therefore higher hole densities/diameters require a relatively larger thickness for the first portion of the mesh 16. Thus the thickness of the first portion of the mesh 16 is determined by the required mass per unit area and is a function of the material used to form the first portion and the size and shape of the holes in the first portion. As an example, for a first portion made from stainless steel with holes with a uniform diameter of 30 µm that are arranged in a regular hexagonal pattern spaced 50 µm apart, a stainless steel layer that is 100 µm thick will meet the mass requirement.

In addition to the laser drilling and electroformation techniques described above, those skilled in the art will be aware of other techniques that can be used to create the first portion and/or the holes in the first portion.

Then, in step 103, a second material of lower density than the first material is used to form a second portion of the mesh 16, with the second portion forming the nozzles at the outlet side 20 of the mesh 16. The second material is a material that allows fabrication techniques to be used that have sufficient precision to form nozzles with the required exit diameter and tolerance in the second material (e.g. 2.5 µm±0.065 µm). The second material can be silicon, a polymer or an epoxy. Suitable polymers include polycarbonate and polyimide, and a suitable epoxy is Epo-tek® 353ND. The second portion of the mesh 16 can have a thickness that is greater than 5 µm and/or less than 20 µm. In an example, the thickness is in the range of 5 to 20 µm. In general, materials having a density greater than 0.8 g/cm$^3$ and/or less than 3 g/cm$^3$ are suitable for use in forming the second portion of the mesh 16. In an example, materials having a density in the range of 0.8 to 3 g/cm$^3$ are used for forming the second portion of the mesh 16.

Different ways of implementing step 103 will be described in more detail below.

In an example (not further shown in detail), the step of providing a first portion made of the first material having the plurality of holes formed therethrough comprises:

providing the plurality of holes in the first portion made of the first material as first openings forming inlet openings of the mesh.

The step of using a second portion made of the second material having the plurality of holes formed therethrough comprises:

providing the plurality of holes in the second portion made of the second material as second openings forming the nozzles with outlet openings of the mesh.

The second portion provides transition portions between the inlet openings and the outlet openings. Further the outlet openings are smaller than the inlet openings.

In another example (also not further shown in detail), in step b), the second openings forming the nozzles are provided having a tapered cross-section with a decreasing width in flowing direction. In step b), the second material is provided with an increasing material thickness forming the nozzle openings.

In a further example (also not further shown in detail), in step a), the plurality of holes in the first portion made of the first material is provided with a first hole geometry having a first opening size. In step b), the plurality of holes in the second portion made of the second material is provided with a second hole geometry having a second opening size; wherein the second opening size is smaller than the second opening size.

In step a), the plurality of the holes in the first portion provides first supply openings.

In step b), the plurality of holes in the second portion provides the nozzles as second outlet openings that are arranged stream-downwards from the first supply openings.

In a still further example (not shown), the first material is provided as a layer or plate comprising the plurality of holes. The second material is provided as a plurality of inlays that are least partly located in the holes of the first portion, each inlay at partly filling one of the holes in the first material, and having the nozzles formed in the second material.

Figure 5:
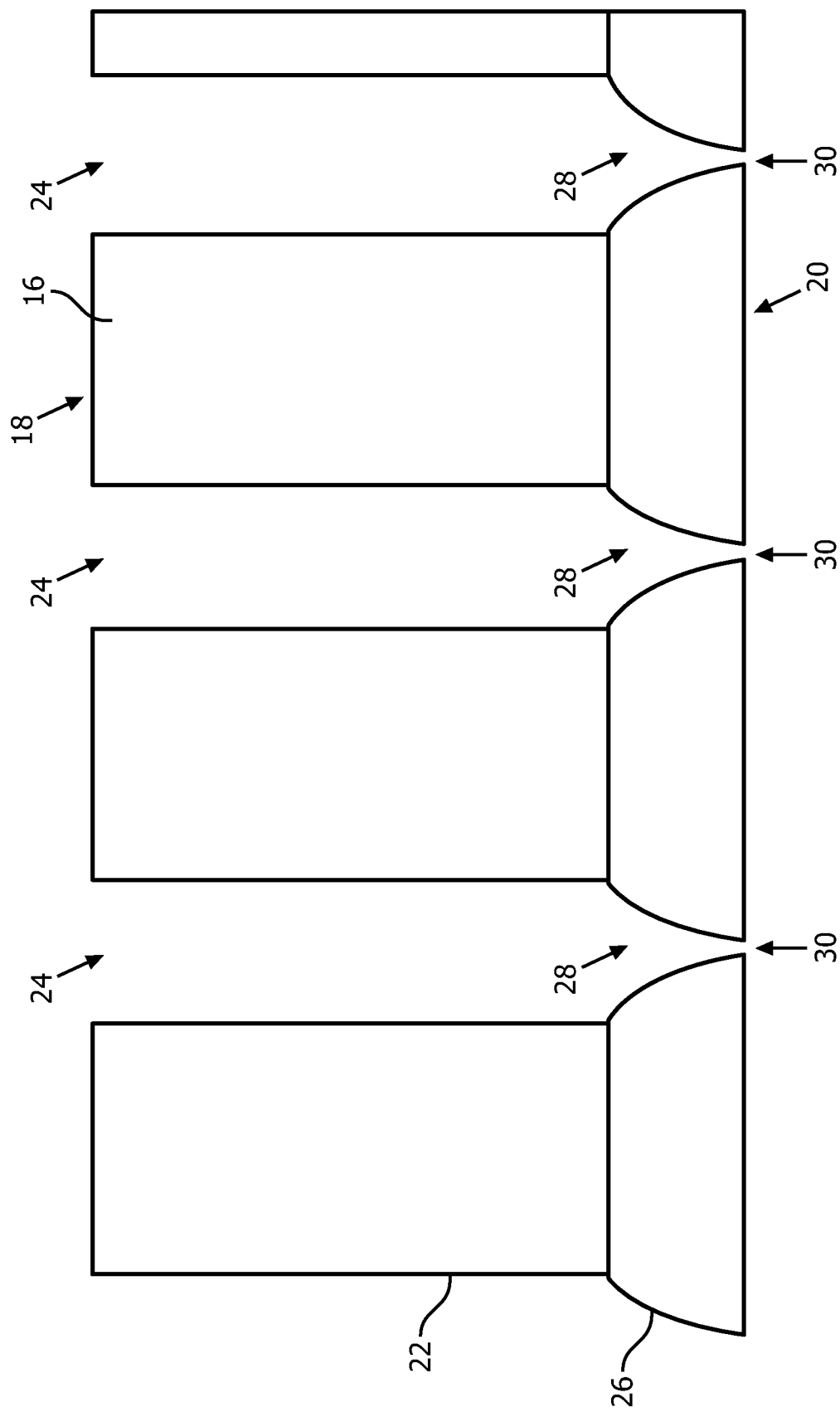
FIG. 5 is a cross-section through a mesh according to a first embodiment of the invention.
Figure 12:
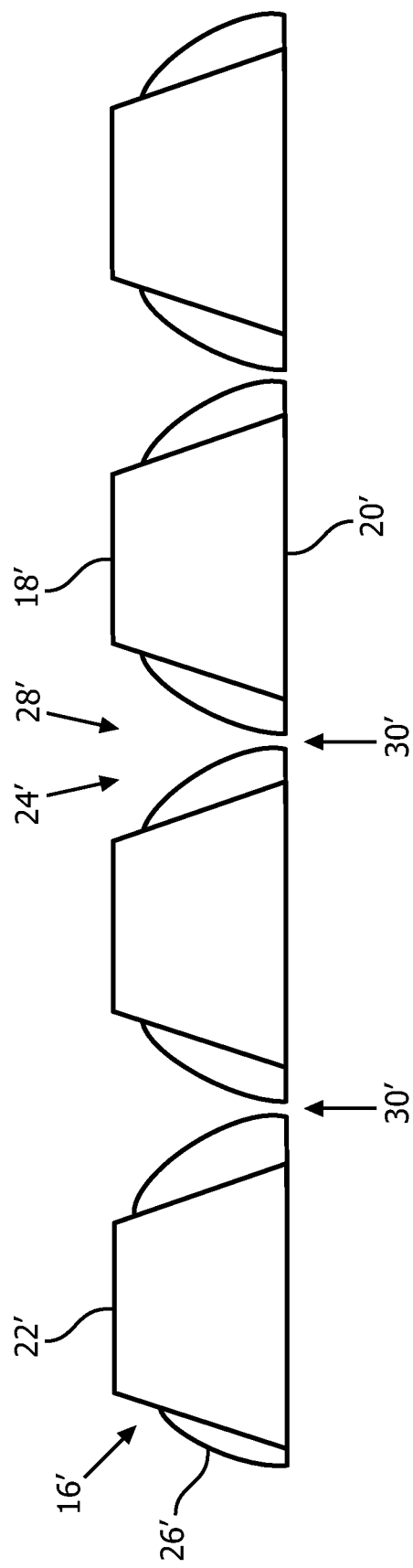
FIG. 12 is a cross-section through a mesh according to a second embodiment of the invention.

In an example, a mesh 16 is provided with the plurality of holes in the first portion made of the first material are first openings forming inlet openings of the mesh. For example, in FIG. 5, the inlet openings are provided by the upper (in relation to FIG. 5 arranged in a landscape manner) side or end of the holes indicated with 24. In FIG. 12, the inlet openings are also provided by the upper (in relation to FIG. 12 arranged in a landscape manner) side or end of the holes indicated with 24'. The plurality of holes in the second portion made of the second material are second openings forming the nozzles with outlet openings, indicated with 30 in FIG. 5 and 30' in FIG. 12, of the mesh. The second portion thus provides transition portions between the inlet openings and the outlet openings, as shown in FIGS. 5 and 12. As also shown in FIGS. 5 and 12, the outlet openings are smaller than the inlet openings.

In another example, the second openings forming the nozzles are having a tapered cross-section with a decreasing width in flowing direction. This is shown in FIGS. 5 and 12 for the respective two exemplary embodiments. It is noted that the second material is provided with an increasing material thickness forming the nozzle openings. In other words, the second material is used for the actual shaping or forming of the opening channels.

In a further example, the plurality of holes in the first portion made of the first material are provided with a first hole geometry having a first opening size. For example, in FIG. 5, the hole geometry of the first openings is shown with parallel side walls, for example as cylindrical portions in the first material. In FIG. 12, the hole geometry of the first openings is shown with tapering side walls, for example as conical portions in the first material. The plurality of holes in the second portion made of the second material is provided with a second hole geometry having a second opening size. For example, in FIG. 5, the hole geometry of the second openings is shown with a decreasing width in flow direction, which decreasing is provided to a varying degree, e.g. larger degree. For example, in FIG. 12, the hole geometry of the second openings is shown with a decreasing width in flow direction, which decreasing is provided to a varying degree, e.g. larger degree, compared to the opening geometry provided by the first material. As also shown in FIGS. 5 and 12, the second opening size is smaller than the second opening size. The plurality of the holes in the first portion thus provides first supply openings, and the plurality of holes in the second portion provides the nozzles as second outlet openings that are arranged stream-downwards from the first supply openings. According to the invention, the exact size and shape of the outlet openings as the nozzles can be provided by the second material, thus making use of the respective material properties.

FIG. 5 is a cross-section through a mesh 16 manufactured according to a first embodiment of the invention. In this mesh 16, the first portion 22 (made from the first material) is a layer or plate, with the plurality of holes 24 formed therethrough. In the illustrated embodiment, the plurality of holes 24 have a generally uniform diameter through the first portion 22 although other hole profiles are possible. In particular, it is desirable to provide a smooth transition from the holes 24 in the first portion 22 to the holes in the second portion 26, and thus the holes 24 in the first portion 22 preferably taper from the side of the first portion 22 that forms the inlet side 18 of the mesh 16 towards the side that is to be placed in contact with the second portion 26. For example, the holes 24 in the first portion 22 may taper from a diameter of 25 µm at the inlet side 18 of the first portion 22 to a diameter of 15 µm at the interface side of the first portion 22 (i.e. the side that is opposite the inlet side 18 and that contacts the second portion 26).

As noted above, one side of the first layer 22 forms the inlet side 18 of the mesh 16. The other (interface) side of the first layer 22 is in contact with the second portion 26 (made from the second material) that is in the form of a layer or plate 26. The opposite side of the second portion 26 (i.e. the side opposite the side that interfaces with or contacts the first portion 22) forms the outlet side 20 of the mesh 16. The second portion 26 has a plurality of nozzles 28 corresponding to the plurality of holes 24 in the first portion 22 (i.e. a plurality of nozzles 28 that generally align with the holes 24 in the first portion 22), such that the each hole 24 and corresponding nozzle 28 form a path for liquid to pass from the inlet side 18 of the mesh 16 to the outlet side 20.

The nozzles 28 in the second portion 26 are formed such that their diameter narrows from generally the same diameter as the holes 24 at the interface side (i.e. the side opposite the inlet side 18) of the first portion 22 to the desired exit diameter at the outlet side 20 of the mesh 16. Preferably there should be no substantial discontinuity between the diameter of the holes 24 in the first portion 22 and the nozzles 28 in the second portion 26 at the interface between the first portion 22 and the second portion 26 as discontinuities can reduce the droplet generation performance of the mesh 16. The exit of the nozzles 28 is denoted 30 in FIG. 5. The profile of each nozzle 28 can taper to the desired diameter for the nozzle exit 30 in a linear or non-linear fashion (so producing a nozzle 28 with a straight or curved profile).

In an example, the first material is provided as a first layer or plate comprising the plurality of holes. The second material is provided as a second layer or plate, in which the nozzles are formed, as shown in FIG. 5.

Figure 6:
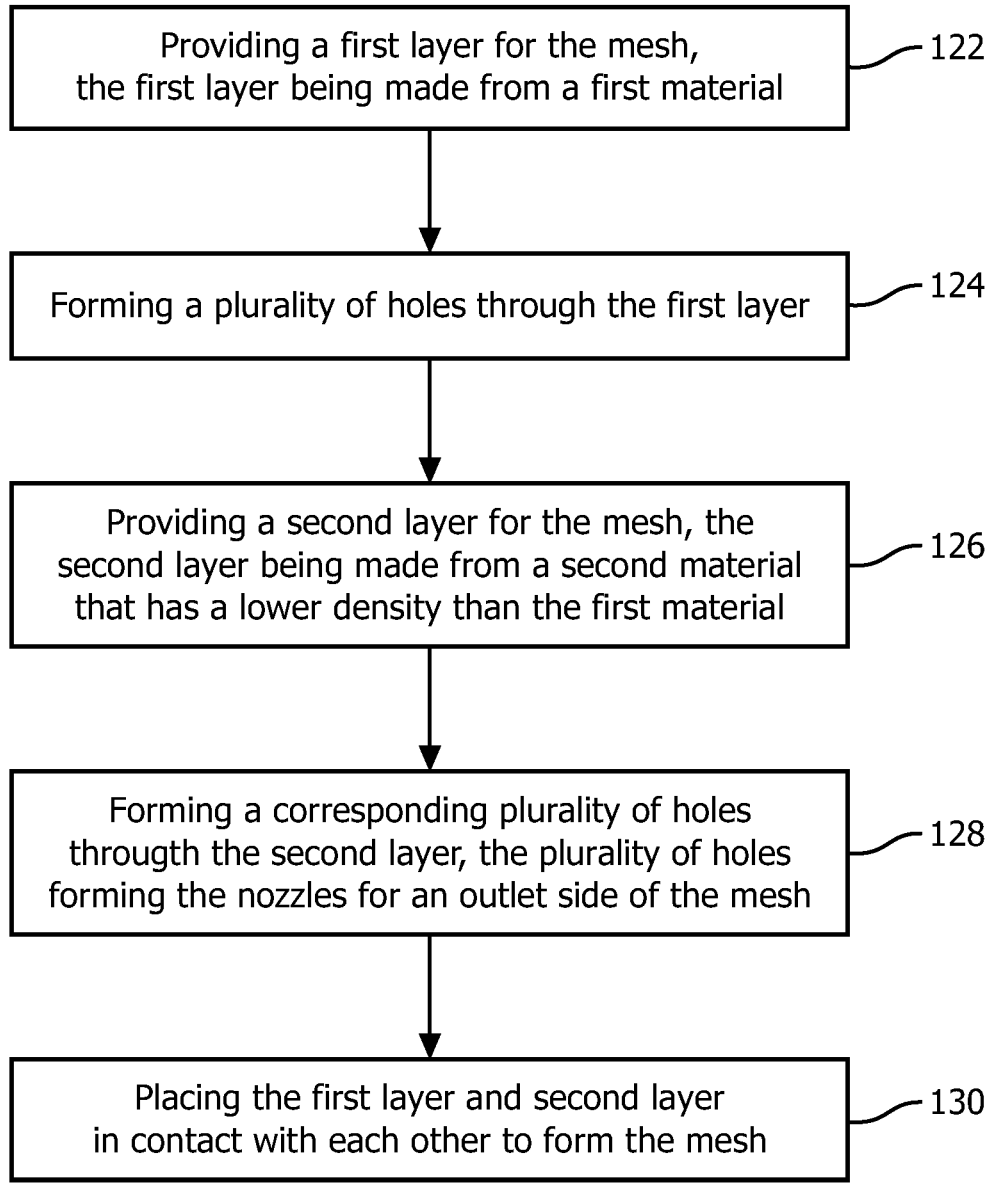
FIG. 6 is a flow chart illustrating a method of manufacturing a mesh according to the first embodiment.
Figure 7A:
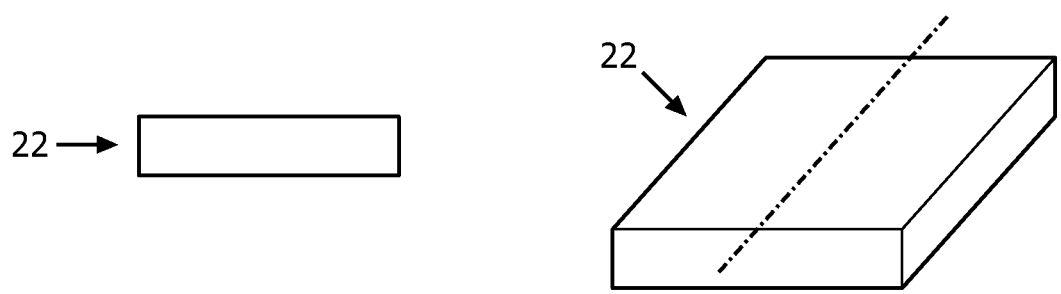
FIG. 7 illustrates the steps in the method of FIG. 6.
Figure 7B:
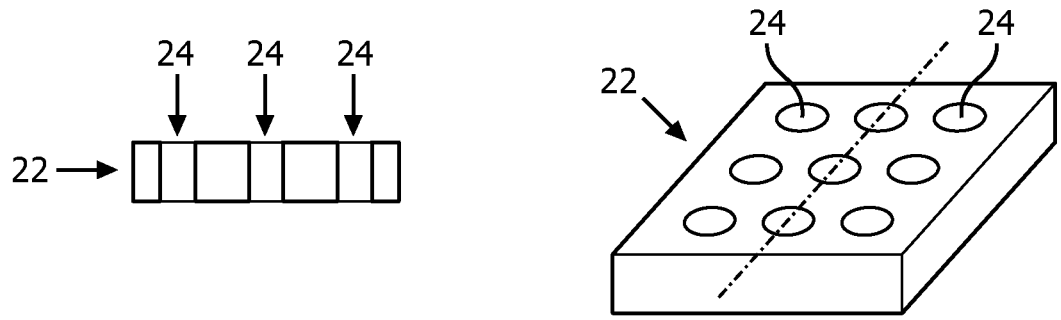
Figure 7C:
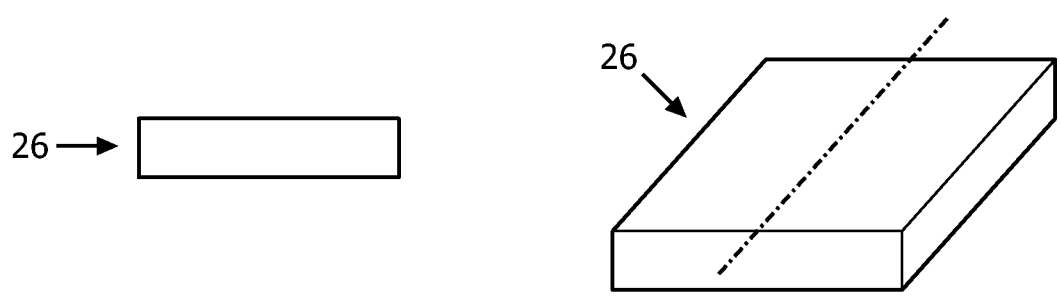
Figure 7D:
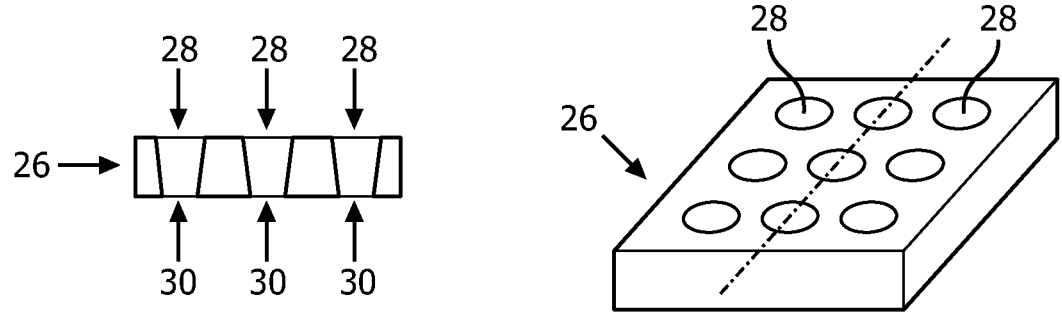
Figure 7E:
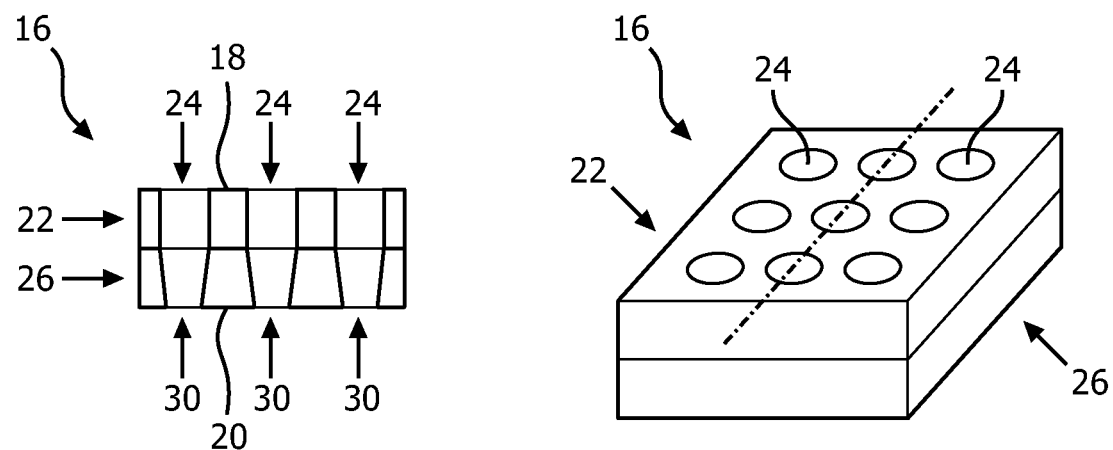

The flow chart in FIG. 6 illustrates an exemplary method of manufacturing a mesh 16 according to the first embodiment as shown in FIG. 5. FIGS. 7(*a*)-(*e*) illustrate the steps in the method of FIG. 6.

Thus, in a first step, step 122, and as shown in FIG. 7(*a*), a first portion 22 in the form of a layer of a first material is provided. As noted above, the first material is selected in order to provide the mass required for the mesh 16 to form the resonant cavity with the nebulisation chamber 10 and actuator 14. The first material in this embodiment is preferably a metal or metal alloy, for example stainless steel, platinum or nickel palladium. Those skilled in the art will be aware of suitable techniques like electroforming or laser drilling/etching) for forming the first portion from the first material, and those techniques will not be described herein.

Figure 8:
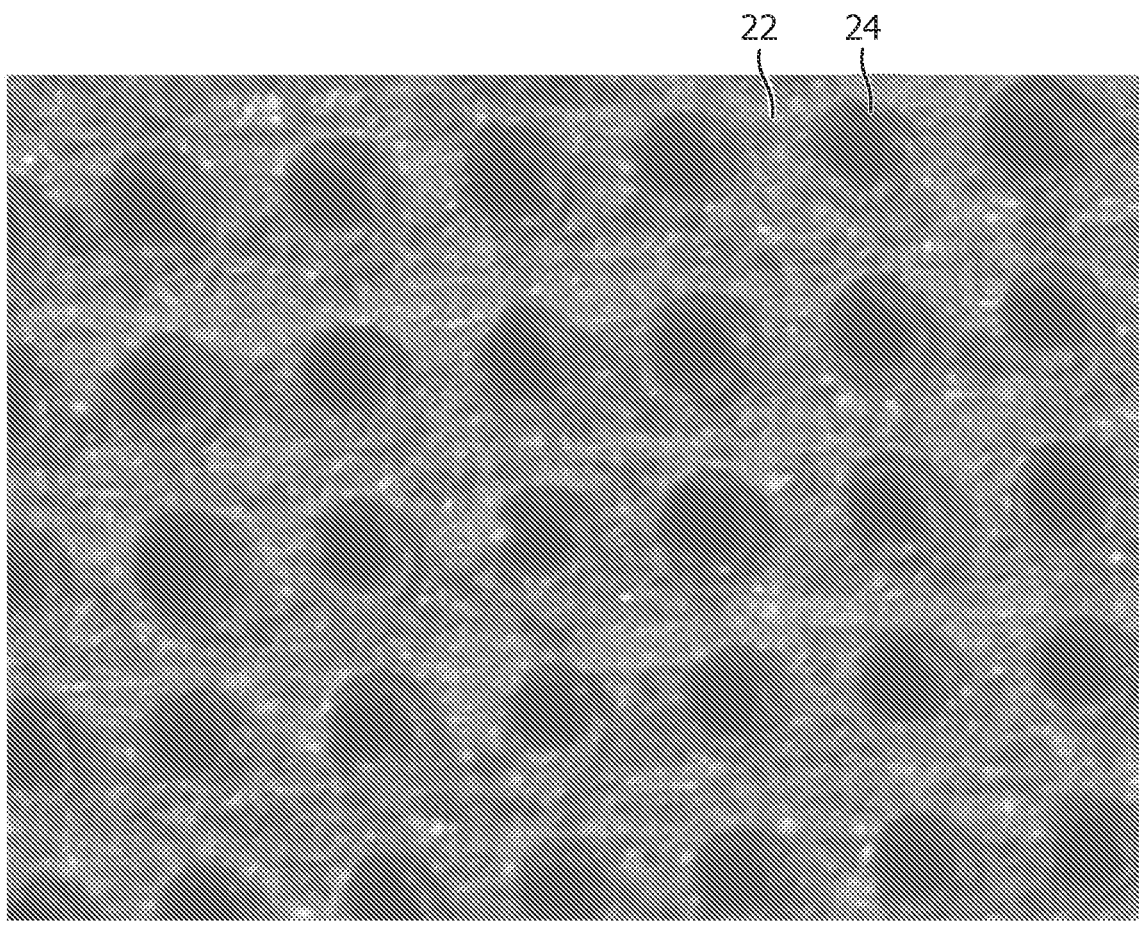
FIG. 8 is an image of holes drilled into stainless steel.

Next, in step 124, and as shown in FIG. 7(*b*), a plurality of holes 24 are formed through the first portion 22. As noted above, where the first portion 22 is made from stainless steel, the plurality of holes 24 can be formed using laser drilling. FIG. 8 is a magnified image of a stainless steel plate in which holes 24 have been laser-drilled (although it should be noted that the holes 24 in this plate taper from a diameter of around 30 µm at the inlet (visible) side 18 to about 10 µm at the interface side). In other embodiments, for example where the first portion 22 is made from platinum or nickel palladium, the holes 24 are created when the first portion 22 is formed by electroformation using electroplating (which effectively reduces the steps described in step 122 and 124 and as shown in FIGS. 7(*a*) and (*b*) to a single step as shown in FIG. 4).

In step 126, and as shown in FIG. 7(*c*), a second portion 26 in the form of a layer or plate of a second material is provided. As noted above, the second material is selected to allow manufacturing techniques to be used to form nozzles in the second portion 26 having the required exit diameter. The second material in this embodiment is preferably silicon or a polymer. Those skilled in the art will be aware of suitable techniques for forming the second portion from the second material, for example using photolithography to define the holes, and those techniques will not be described herein.

Figure 9:
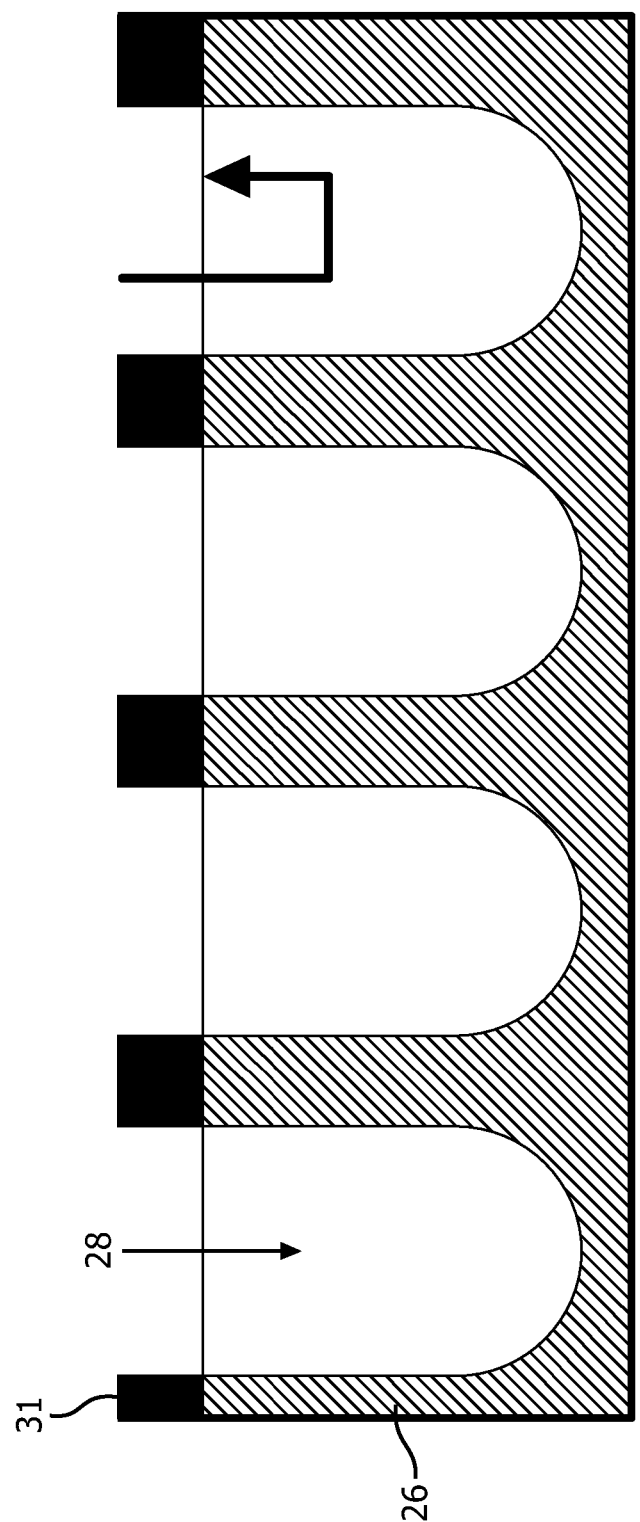
FIG. 9 illustrates the general principles of chemical etching.
Figure 10:
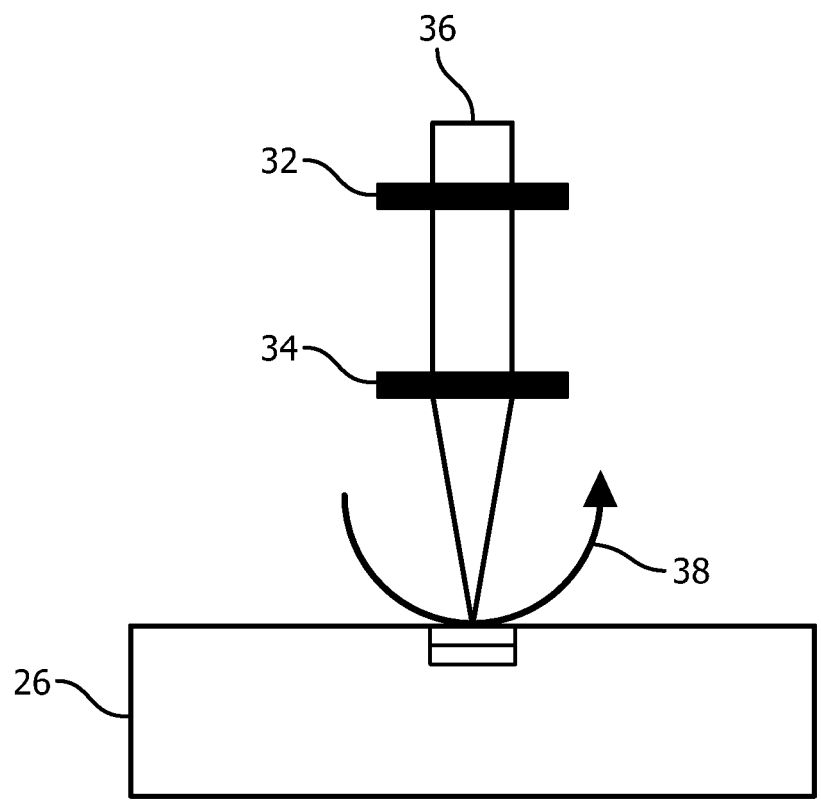
FIG. 10 illustrates the general principles of laser etching.
Figure 11B:
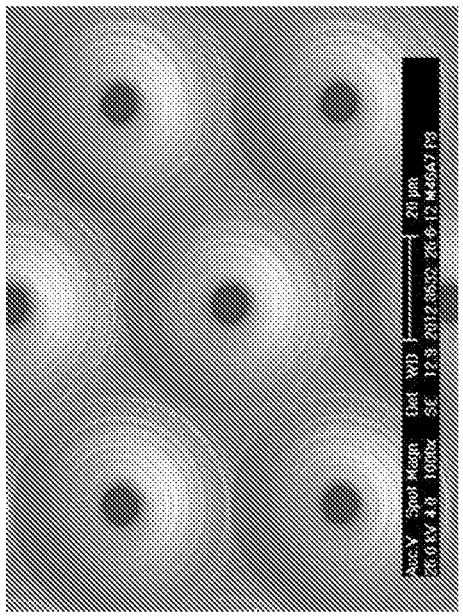
FIG. 11 shows various images of nozzles that have been laser-etched into polycarbonate.
Figure 11A:
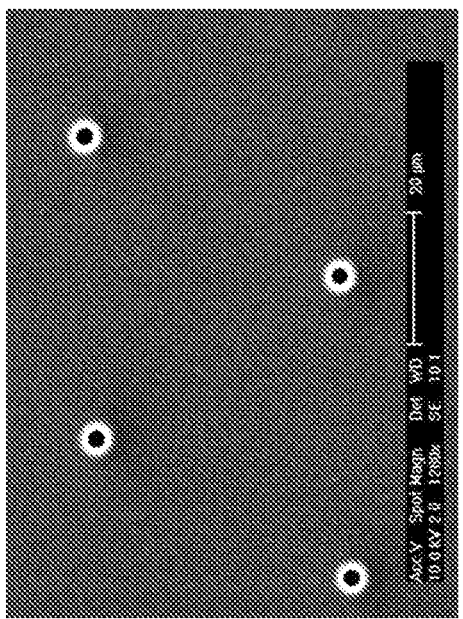
Figure 11D:
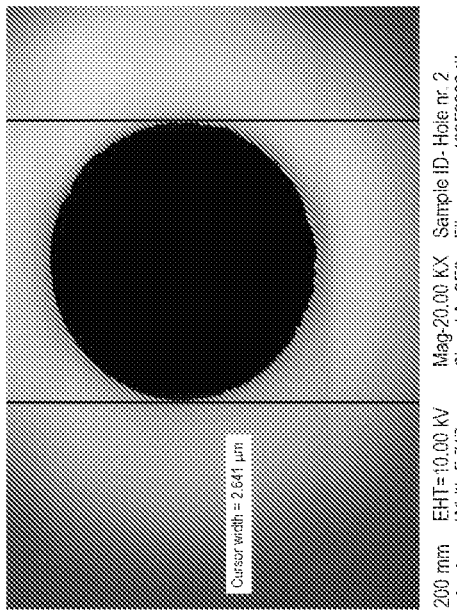
Figure 11C:
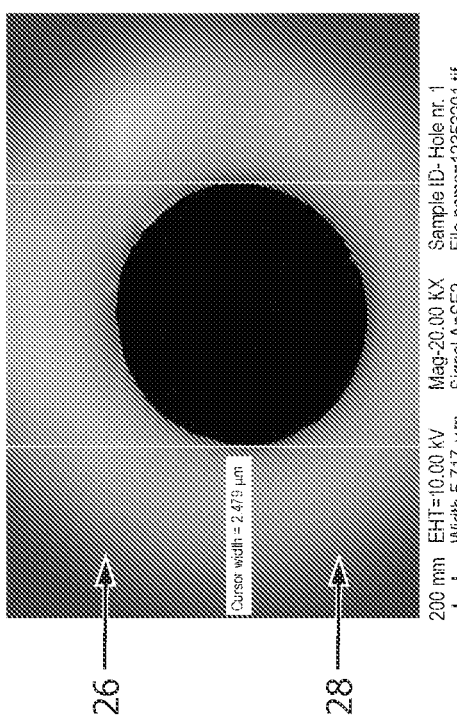

In step 128, and as shown in FIG. 7(*d*), a plurality of nozzles 28 are formed through the second portion 26, with the diameter of the nozzles 28 at one side of the second portion 26 being approximately equal to the diameter of the holes 24 in the interface side of the first portion 22 (to avoid or reduce discontinuities), and the diameter of the nozzles 28 at the other side of the second portion 26 being the required size to within the required tolerance (e.g. 2.5 µm±0.065 µm).

Where the second material is silicon, the nozzles 28 can be formed in the second portion 26 using chemical etching. Although techniques for chemical etching in silicon are well-known in the art and will not be described in detail herein, FIG. 9 illustrates the general principles of chemical etching. In particular, a resist 32, which is a template in which the desired nozzle pattern is formed, is placed over the second portion 26 to protect parts of the second portion 26 that are not to be etched. A chemical solvent is applied to the exposed parts of the second portion 26 (i.e. the parts not protected by the resist 31) which dissolves the second material and forms the nozzles 28.

Where the second material is a polymer, the nozzles 28 can be formed in the second portion 26 using laser etching. Although techniques for laser etching in polymers (which is also known as laser machining or laser processing) are well-known in the art and will not be described in detail herein, FIG. 10 illustrates the general principles of laser etching. In particular, a mask 32, which is a template in which the desired nozzle pattern is formed, is placed over the second portion 26, along with a lens 34, and laser light 36 is shone through the mask 32 and lens 34 onto the second portion 26. The laser light etches away/vaporises the exposed parts of the second portion 26 (i.e. the parts not covered by the mask 32) to form the nozzles 28. A gas flow 38 is provided to remove the second material that is vaporised by the laser light 36. Typically an excimer laser having a wavelength of 150-400 nm is used, with the laser being pulsed to remove around 0.15 µm of material from the second portion 26 per pulse.

The images in FIG. 11 show various views (at various magnification levels) of nozzles 28 that have been laser-etched into a polymer (in particular polycarbonate).

Once the first portion 22 and the second portion 26 have been fabricated, the portions 22 and 26 are placed in contact with each other to form the mesh 16 with each hole 24 in the first portion 22 generally aligning with a nozzle 28 in the second portion 26 (step 130 and FIG. 7(*e*)). In particular embodiments, the first portion 22 is bonded or attached to the second portion 26 using an adhesive or adhesive film, although care should be taken to avoid the adhesive from entering the holes 24 or nozzles 28.

It will be appreciated that steps 122 to 128 shown in FIG. 6 do not need to be performed in the illustrated order, and in some implementations steps 128/130 can be performed before or at generally the same time as steps 122/124.

FIG. 12 is a cross-section through a mesh 16' manufactured according to a second embodiment of the invention. In this mesh 16', the first portion 22' (made from the first material) comprises a layer or plate, with the plurality of holes 24' formed therethrough. In this embodiment of the invention, the thickness of the first portion 22' can be greater than 5 μm and/or less than 30 μm. In an exemplary implementation of the second embodiment, the thickness of the first portion 22' is in the range 5 to 30 μm. In the illustrated embodiment, the diameter of the holes 24' taper in from the top of the first portion 22' (corresponding to the inlet side 18' of the mesh 16') towards the outlet side 20' of the mesh 16'. In alternative embodiments, the diameter of the holes 24' can be uniform through the first portion 22' (i.e. with no tapering).

As noted above, one side of the first layer 22' forms the inlet side 18' of the mesh 16'. In this embodiment, the other side of the first layer 22' forms part of the outlet side 20' of the mesh 16'. The first portion 22' is in contact with the second portion 26' (made from the second material). In this embodiment, the second material is used to fill the holes 24', and then nozzles 28' are formed in the second material, with the diameter of the nozzles 28' in second material at the outlet side 20' of the mesh 16' having the required size and tolerance (e.g. 2.5 μm±0.065 μm). The exit of the nozzles 28' is denoted 30' in FIG. 12. The profile of each nozzle 28' can taper to the desired diameter for the nozzle exit 30' in a linear or non-linear fashion (so producing a nozzle 28' with a straight or curved profile).

In an example, the first material is provided as a layer or plate comprising the plurality of holes. The second material is provided as a plurality of inlays that are least partly located in the holes of the first portion, each inlay at partly filling one of the holes in the first material, and having the nozzles formed in the second material, as shown in FIG. 12.

Figure 13:
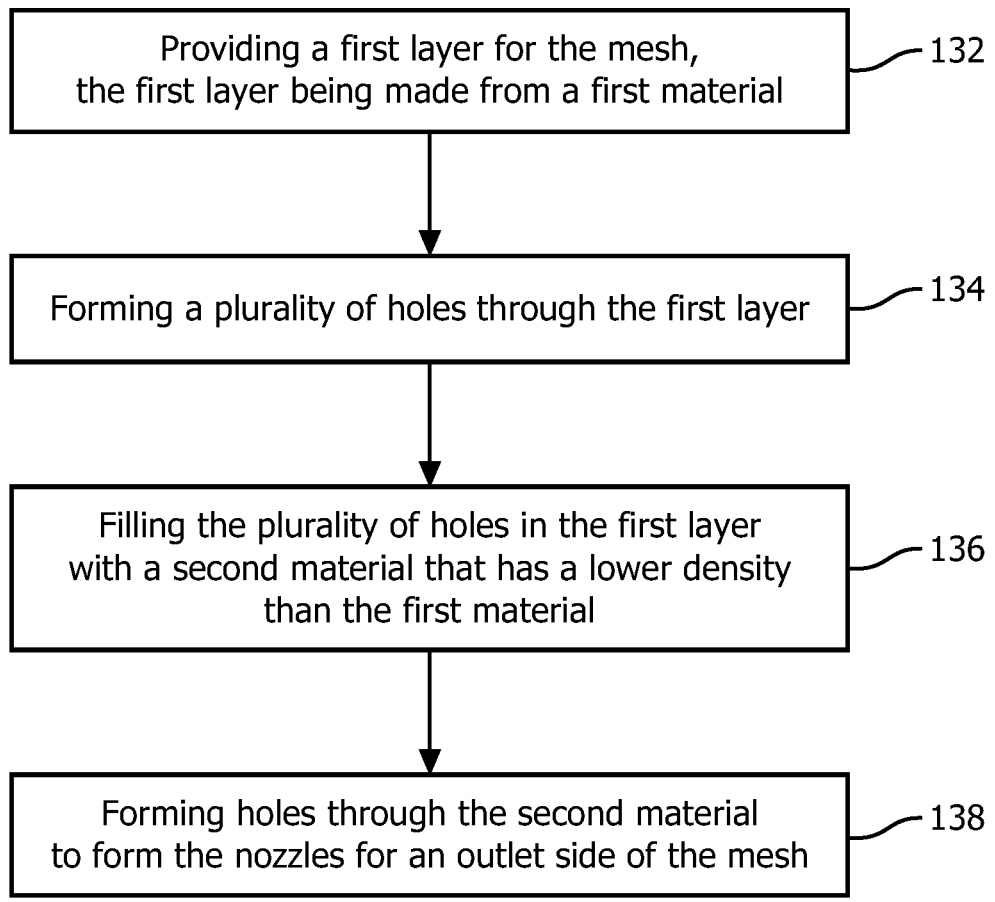
FIG. 13 is a flow chart illustrating a method of manufacturing a mesh according to the second embodiment.

The flow chart in FIG. 13 illustrates an exemplary method of manufacturing a mesh 16' according to the second embodiment as shown in FIG. 12. FIGS. 14(a)-(d) illustrate the steps in the method of FIG. 13.

Steps 132 and 134 are similar to steps 122 and 124 shown in FIG. 6 and as described above.

Figure 14A:
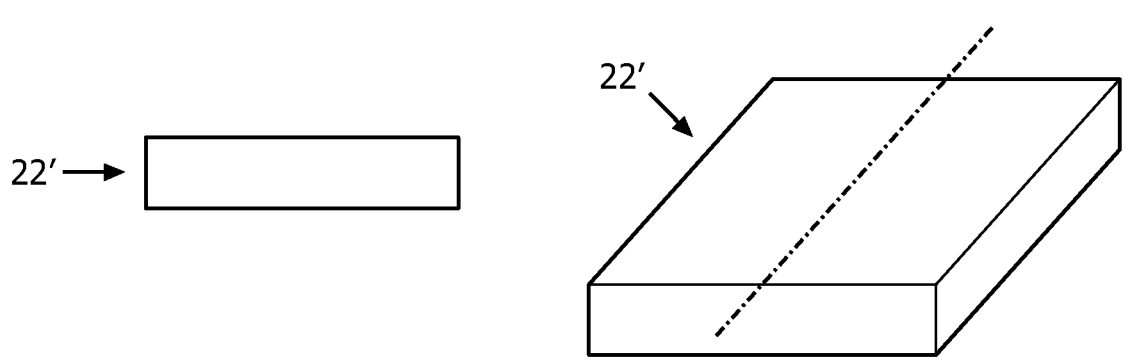
FIG. 14 illustrates the steps in the method of FIG. 13.
Figure 14B:
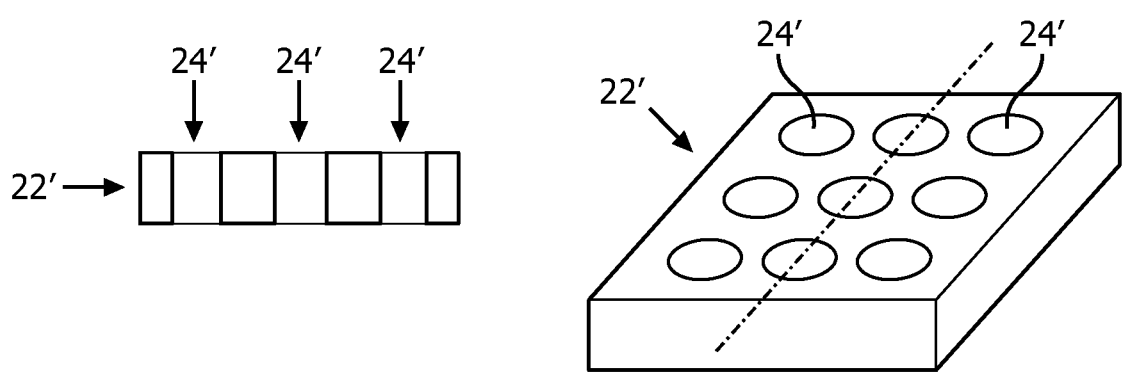
Figure 14C:
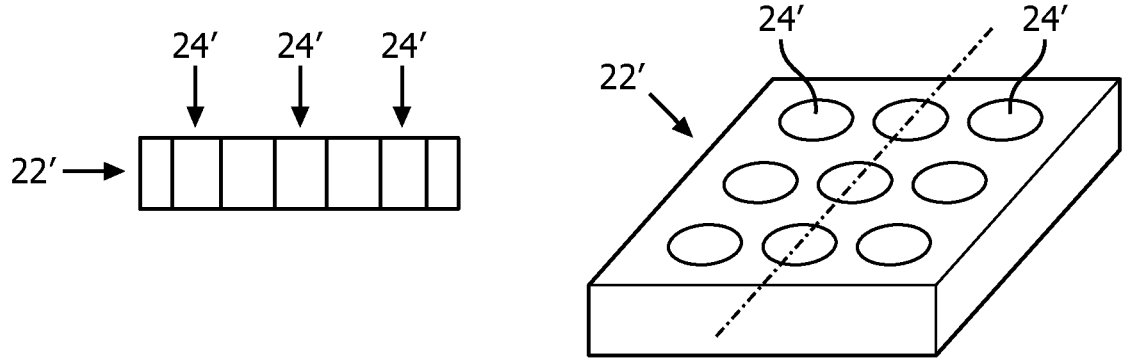

Once the plurality of holes 24' have been formed in the first portion 22', the holes 24' are filled with the second material (step 136 and as shown in FIG. 14(c)). In this embodiment the second material can be an epoxy or liquid polymer that can be poured into the holes 24' and that sets to form the second portion 26'.

The images in FIG. 15(a)-(d) show a metal foil 22' with holes 24' filled with a medical grade epoxy 26' at various levels of magnification.

Figure 14D:
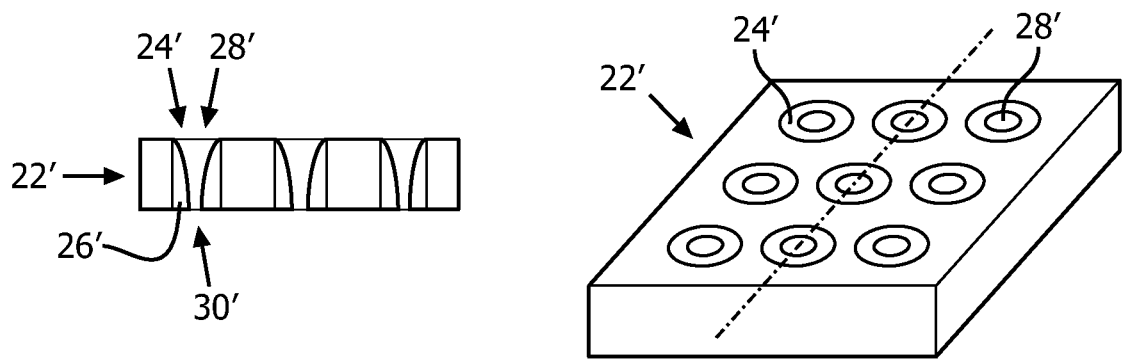
Figure 15A:
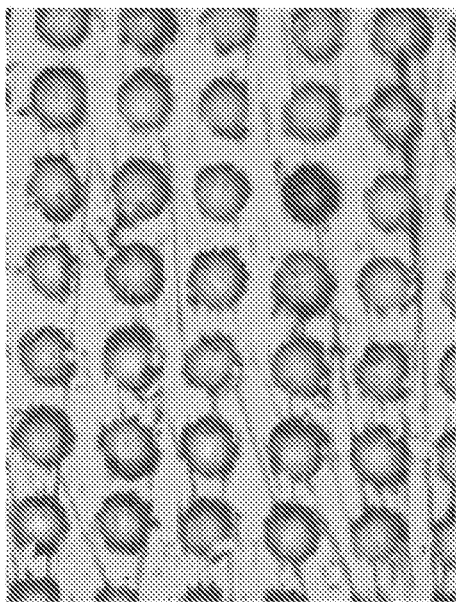
FIG. 15 shows various images illustrating the steps in the method of FIG. 13.
Figure 15B:
Figure 15C:
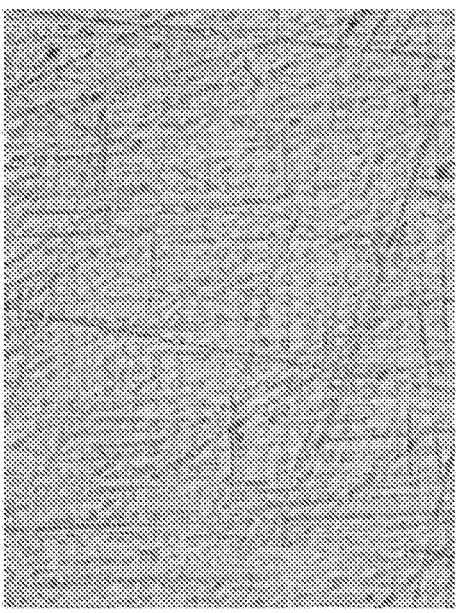
Figure 15D:
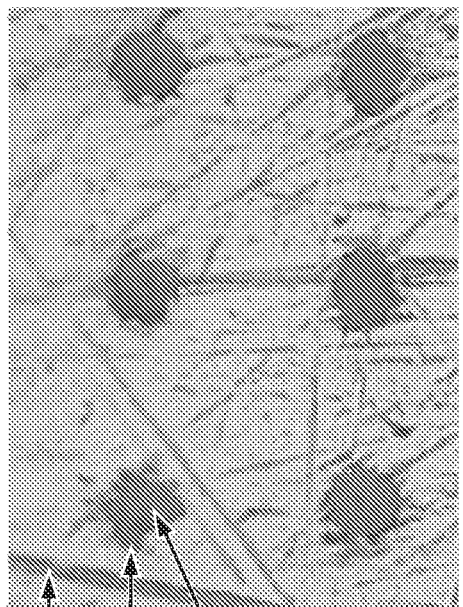
Figure 15E:
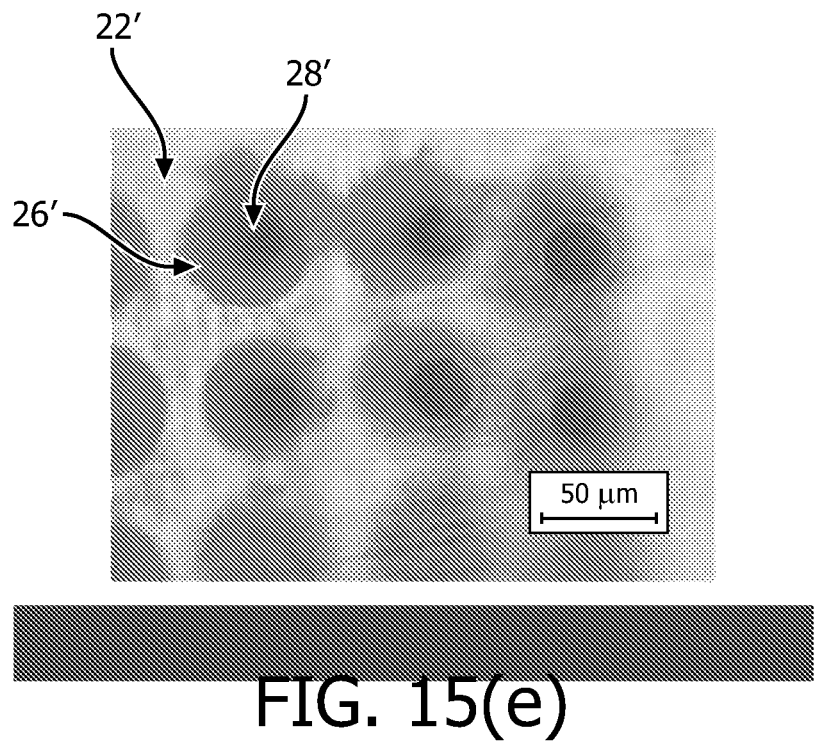
Figure 15F:
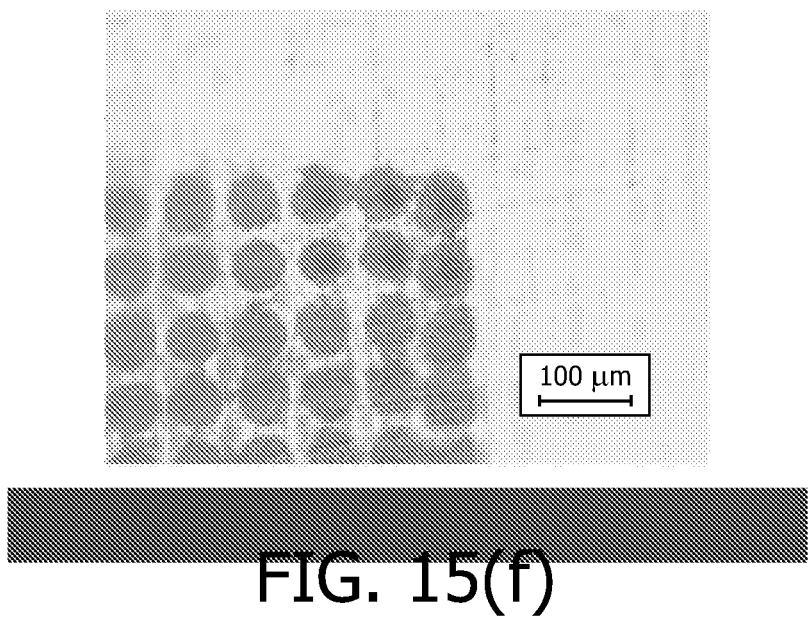

Next, in step 138 (and as shown in FIG. 14(d)), holes are made through each of the portions 26' of the second material to form the nozzles 28' for the outlet side 20' of the mesh 16'. As in the first embodiment, the holes/nozzles 28' can be made using chemical etching or laser etching. Alternatively, the holes/nozzles 28' can be made using laser drilling. FIGS. 15(e) and (f) show the metal foil from FIGS. 15(a)-(d) with nozzles 28' that have been laser drilled in the second material.

After the holes/nozzles 28' have been formed, the mesh 16' is complete.

There is therefore provided a mesh that has a tight tolerance on nozzle exit diameter and the mass required to create a resonant cavity in a nebuliser that can be manufactured at lower cost through a higher yield manufacturing process.

In an example, a nebulizer is provided with a similar design as the nebulizer shown in FIG. 1. The nebulizer comprises a body having an inlet and an outlet arranged so that when a user of the nebuliser inhales through the outlet, air is drawn into and through the nebuliser via the inlet and outlet and into the user's body. The outlet may be provided in the form of a mouthpiece or a facial or nasal mask or in a form that is suitable for connection to a separate replaceable mouthpiece or facial or nasal mask. Further, a nebulisation chamber is provided between the inlet and outlet for storing a liquid. The nebuliser is configured such that the fine droplets of liquid combine with the air drawn through the nebuliser when the user inhales to deliver a dose of the medication or drug to the user. For this reason, a mesh is provided as described in more detail above.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are recited in mutually different dependent claims does not indicate that a combination of these measures cannot be used to advantage. Any reference signs in the claims should not be construed as limiting the scope.

The invention claimed is:

1. A method of manufacturing a mesh for use in forming droplets of liquid medicine in a nebulizer, the method comprising: a) providing a first portion made of a first material having a plurality of holes formed therethrough as an inlet side of the mesh; b) filling the plurality of holes of the first portion using a second portion made of a second material that has a lower density than the first material to thereafter form nozzles for an outlet side of the mesh; and, c) thereafter forming the nozzles, by removing part of the second material of the second portion to create a plurality of holes in the second portion aligned with the plurality of holes of the first portion, with the plurality of holes in the second portion each having exit diameters of less than the respective diameters of the plurality of holes of the first portion; wherein the plurality of the holes in the first portion provide supply openings for a liquid medicine, wherein the plurality of holes in the second portion provide the nozzles as outlet openings for droplets of the liquid medicine, wherein the outlet openings are arranged downstream from the supply openings and wherein the mesh has sufficient mass to create a resonant cavity in the nebulizer.

2. The method as claimed in claim 1, wherein the step of providing the first portion made of the first material having the plurality of holes formed therethrough comprises:

a1) providing the first portion made of the first material; and a2) forming the plurality of holes through the first portion.

3. The method as claimed in claim 1, wherein the removing part of the second material of the second portion provides the nozzles with an increasing material thickness; in step a), the plurality of holes in the first portion made of the first material are provided with a first hole geometry having a first opening size, wherein, in step b), the plurality of holes in the second portion made of the second material are provided with a second hole geometry having a second opening size, wherein the second opening size is smaller than the first opening size.

4. The method as claimed in claim 1, wherein first portion further comprises:

a layer or plate.

5. The method of claim 1, wherein the plurality of holes in the second portion are formed using one or more of laser drilling, laser etching or chemical etching.

6. The method of claim 1, wherein the plurality of holes in the second portion have diameters of equal to substantially 2.5 μm.

7. The method of claim 1, wherein the plurality of holes in the second portion have diameters selected to produce droplets of liquid medicine having an upper limit of mass median diameter (MMD) of 5 μm.

8. The method of claim 1, comprising selecting the second material to produce a desired diameter of the plurality of holes in the second portion.

9. A nebulizer, comprising: a body having an inlet and an outlet arranged to deliver a liquid medication to a user; a chamber configured to hold the liquid medicine to be nebulized and comprising the mesh formed by the method of claim 1; and a piezoelectric element configured to nebulize the liquid medicine; the mesh being configured to produce droplets of the liquid medicine having an upper limit of mass median diameter (MD) of 5 μm.

10. The nebulizer of claim 9, wherein the exit diameters is 2.5 μm.

11. The nebulizer of claim 9, wherein the piezoelectric element is a plate and positioned opposite the mesh.

12. The nebulizer of claim 9, wherein the plurality of holes in the second portion are laser or chemical etched or laser drilled holes.

* * * * *